United States Patent [19]

McKenzie et al.

[11] 4,221,715

[45] Sep. 9, 1980

[54] SUBSTITUTED DIBENZ[b,f][1,4]OXAZEPIN-11-YL PYRIDINIUM SALTS AND DERIVATIVES THEREOF

[75] Inventors: Thomas C. McKenzie, Pearl River, N.Y.; Lantz S. Crawley, Clifton, N.J.; John J. Brown, Pearl River, N.Y.

[73] Assignee: American Cyanamid Company, Stamford, Conn.

[21] Appl. No.: 63,482

[22] Filed: Aug. 3, 1979

[51] Int. Cl.$^2$ .................... C07D 413/02; C07D 413/14
[52] U.S. Cl. ............................... 260/244.4; 568/585; 546/298; 424/263

[58] Field of Search ...................... 546/270; 260/244.4

[56] References Cited

PUBLICATIONS

Chemical Abstracts, vol. 79, abst. 18780v (1973), (abst. of Fr. Pat. No. 1,602,883).

*Primary Examiner*—John D. Randolph
*Attorney, Agent, or Firm*—Thomas M. Saunders

[57] ABSTRACT

Substituted Dibenz[b,f][1,4]oxazepin-11-yl pyridinium salts and derivatives thereof useful as intermediates in the preparation of anti-psychotic agents.

14 Claims, No Drawings

SUBSTITUTED DIBENZ[b,f][1,4]OXAZEPIN-11-YL PYRIDINIUM SALTS AND DERIVATIVES THEREOF

SUMMARY OF THE INVENTION

This invention is concerned with compounds of the formula:

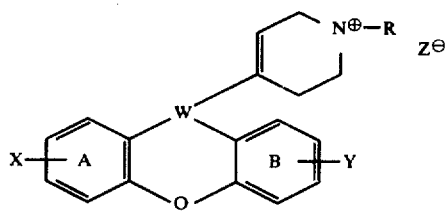

wherein phenyl rings A and B may be unsubstituted, mono-, di- or trisubstituted and X and Y are each selected from the group consisting of hydrogen, halogen, lower alkyl ($C_1$-$C_6$), lower alkoxy ($C_1$-$C_6$), methylthio, trifluoromethyl, nitro, amino and di(lower)alkylsulfamoyl; Z is selected from the group consisting of chlorine, bromine, and iodine; R is selected from the group consisting of lower alkyl ($C_1$-$C_6$), hydroxy lower alkyl, propargyl,

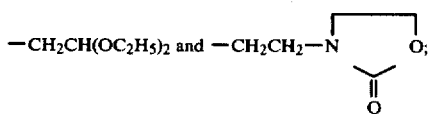

W is selected from the group consisting of

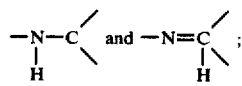

and the pharmaceutically acceptable salts thereof.

More specifically, this invention is concerned with compounds of the formulae:

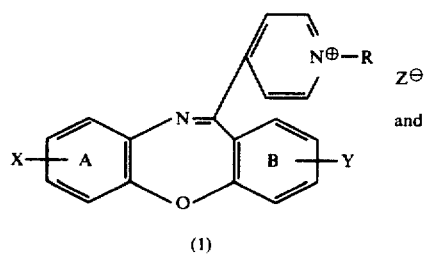

(1)

and

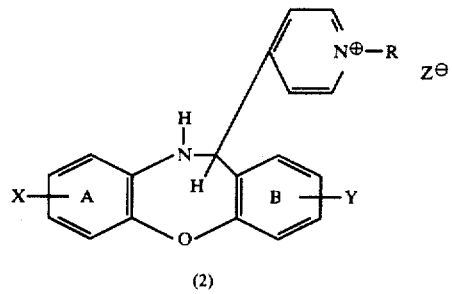

(2)

wherein phenyl rings A and B may be unsubstituted, mono-, di- or trisubstituted and X and Y are each selected from the group consisting of hydrogen, halogen, lowerlakyl ($C_1$-$C_6$), lower alkoxy ($C_1$-$C_6$), methylthio, trifluoromethyl, nitro, amino and di(lower)alkylsulfamoyl; Z is selected from the group consisting of chlorine, bromine and iodine; and R is selected from the group consisting of lower alkyl ($C_1$-$C_6$), hydroxy lower alkyl, propargyl,

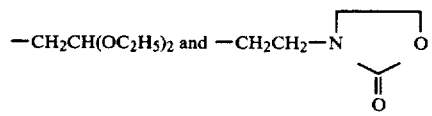

The compounds of the present invention are useful as intermediates in the preparation of the anti-psychotic compounds of U.S. patent appln. Ser. No. 63,481, filed on even date herewith of the formula:

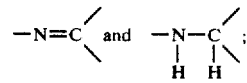

wherein phenyl rings A and B may be unsubstituted, mono-, di- or trisubstituted and X and Y are each selected from the group consisting of hydrogen, halogen, lower alkyl ($C_1$-$C_6$), lower alkoxy ($C_1$-$C_6$), methylthio, trifluoromethyl, nitro, amino and di(lower)alkylsulfamoyl; R is selected from the group consisting of lower alkyl ($C_1$-$C_6$) and hydroxy lower alkyl; W is selected from the group consisting of —N=C and —N—C ;

and the pharmaceutically acceptable salts thereof.

And more specifically, the final products may be represented by the following formulae:

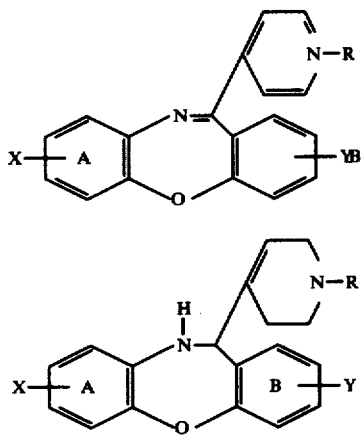

wherein X and Y are as hereinabove described and R is selected from the group comprising lower alkyl ($C_1$–$C_6$), hydroxy lower alkyl, propargyl, —$CH_2$CH($OC_2H_5$)$_2$ and

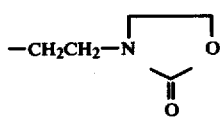

The compounds of the present invention may be prepared according to the following reaction sequence; wherein x, y, and R are as hereinabove described.

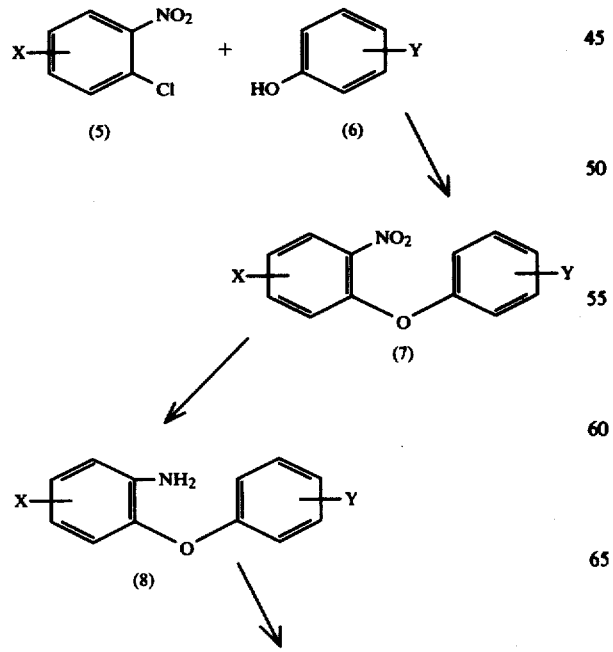

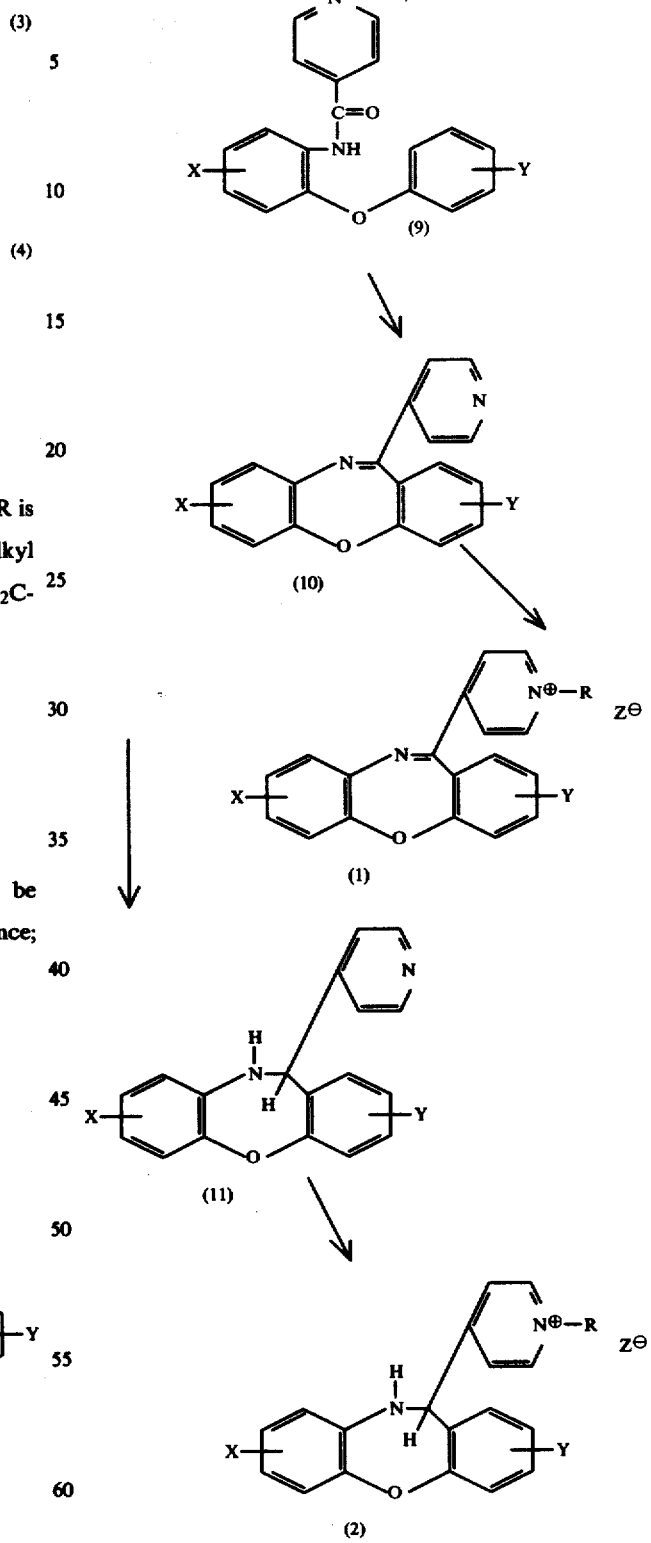

In accordance with this sequence, a 1-chloro-2-nitrobenzene (5) is reacted with a phenol (6) a base such as potassium carbonate and activated copper where necessary in a solvent such as benzene of dimethyl acetamide with heat giving a 2-nitrophenylphenyl ether (7). This ether (7) is then reduced by conventional means (i.e. sodium hydrosulfite) to the phenoxyaniline (8). Isonicotinic acid is reacted with a mineral acid halide such as thionyl chloride heat or by heating at reflux in methylene chloride. The volatiles are evaporated and the residue is reacted with the phenoxyaniline (8) and a base such as triethylamine or potassium carbonate in a solvent such as tetrahydrofuran or benzene at a temperature from 25° to 80° for several hours giving a phenoxyisonicotinanilide (9). This compound (9) is then reacted with phosphorous pentoxide and phosphorous oxychloride at reflux for several hours. The residue is reacted with ammonium hydroxide in ice and extracted in methylene chloride giving an 11-(4-pyridyl)-di-benz[b,f][1,-4]oxazepine (10). This oxazepine (10) is then reacted with an alkyl halide in a solvent such as acetone or methylene chloride to produce (1), where R is as hereinbefore described which is the immediate precursor to the aforementioned anti-psychotic agents. To produce the 10,11-dihydro-11-(4-pyridyl)-dibenz[b,f][1,4]oxazepine (11), the compound (10), is treated with a reducing agent such as an alkali aluminum hydride in a solvent such as ether or benzene at reflux, quenched with water and extracted with methylene chloride. To produce the 10-alkyl-10,11-dihydro-11-(4-pyridyl)-dibenz[b,f][1,-4]oxazepine (11), the compound (10) is dissolved in an alkanoic acid and treated with sodium borohydride. The compound (11) may be converted to the precursor (2) by reactions with an alkyl halide where R is as described above for compound (10).

Among the specific compounds contemplated by the scope of this invention are the following:

8-Chloro-2-methoxy-11-(4-pyridyl)-dibenz[b,f][1,4]oxazepine 4-(8-Chloro-2-methoxydibenz[b,f][1,4]oxazepin-11-yl)-1-methylpyridinium iodide 2,8-Dichloro-11-(4-pyridyl)-dibenz[b,f][1,4]oxazepine 4-(2,8-Dichloro-dibenz[b,f][1,4]oxazepin-11-yl)-1-methylpyridinium iodide 8-Chloro-10,11-dihydro-2-methoxy-11-(4-pyridyl)-dibenz[b,f][1,4]oxazepine 4-(8-Chloro-10,11-dihydro-2-methoxydibenz[b,f][1,-4]oxazepin-11-yl)-1-methylpyridinium iodide 2,8-Dichloro-10,11-dihydro-11-(4-pyridyl)-dibenz[b,f][1,4]oxazepine 4-(2,8-Dichloro-10,11-dihydrodibenz[b,f][1,4]oxazepin-11-yl)-1-methylpyridinium iodide 8-Chloro-11-(4-pyridyl)-dibenz[b,f][1,4]oxazepine 4-(8-Chlorodibenz[b,f][1,4]oxazepin-11-yl-1-methylpyridinium iodide 8-chloro-10,11-dihydro-11-(4-pyridyl)-dibenz[b,f][1,-4]oxazepine 8-Chloro-10-methyl-10,11-dihydro-11-(4-pyridyl)-dibenz[b,f][1,4]oxazepine 4-(10,11-Dihydro-8-chloro-10-methyldibenz[b,f][1,-4]oxazepin-11-yl)-1-methyl-pyridinium iodide

EXAMPLE 1

8-Chloro-2-methoxy-11-(4-pyridyl)-dibenz[b,f][1,4]oxazepine and
4-(8-Chloro-2-methoxydibenz[b,f][1,4]oxazepin-11-yl)-1-methylpyridinium iodide To a mixture of 96.0 g. of 1,4-dichloro-2-nitrobenzene, 62.0 g. of 4-methoxy phenol and one liter of benzene is added 80.0 g. of potassium carbonate and 2.0 g. of activated copper. The mixture is stirred and heated on a steam bath overnight, then filtered and the solvent is removed in vacuo giving 4-methoxyphenyl-4-chloro-2-nitrophenyl ether.

An 80.0 g. portion of the above nitro derivative in 800 ml. of acetone is added to 320.0 g. of sodium hydrosulfite in 800 ml. of water. The mixture is heated to reflux on a steam bath for one hour, cooled and extracted with benzene. The benzene extract is washed with water, dried over anhydrous sodium sulfate and evaporated in vacuo to a yellow oil. Treatment in hexane, with cooling produces crystals of 5-chloro-2-(p-methoxyphenoxy)-aniline.

A mixture of 19.5 g. of isonicotinic acid, 100 ml. of thionyl chloride and 100 ml. of methylene chloride is heated under reflux for 2 hours. The solvent is evaporated, 200 ml. of benzene is added and this solvent is evaporated. To the residue is added 1200 ml. of benzene, 80.0 g. of anhydrous potassium carbonate and 39.0 g. of 5-chloro-2-(p-methoxyphenoxy)-aniline. The mixture is heated under reflux for 8 hours, water is added and the product is extracted in benzene. The benzene extracts are washed, dried and evaporated to a solid residue which is collected with the aid of ether and crystallized from methanol, giving 5'-chloro-2'-(p-methoxyphenoxy)-isonicotinanilide.

A 40.0 g. portion of the preceding compound is added to 50.0 g. of phosphorous pentoxide and 300 ml. of phosphorous oxychloride. The mixture is stirred and heated under reflux for 20 hours, cooled and swamped with ether. The precipitate is collected, washed with ether and added portionwise, with stirring to a mixture of 150 ml. of concentrated ammonium hydroxide and ice. This mixture is extracted with methylene chloride. The extracts are washed, dried and evaporated to a residue. The residue is crystallized from acetone, giving 8-chloro-2-methoxy-11-(4-pyridyl)-dibenz[b,f][1,4]oxazepine, mp. 158°–160° C.

A 10 ml. portion of methyl iodide is added to a solution of 5.0 g. of the preceding compound in 20 ml. of methylene chloride. The mixture is heated under reflux for one hour, ether is added, the precipitate is collected and washed with ether giving 4-(8-chloro-2-methoxydibenz[b,f] [1,4]oxazepin-11-71)-1-methyl-pyridinium iodide, mp. 243°–245° C.

EXAMPLE 2

2,8-Dichloro-11-(4-pyridyl)-dibenz[b,f][1,4]-oxazepine and
4-(2,8-Dichloro-dibenz[b,f][1,4]-oxazepin-11-yl)-1-methylpyridinium iodide A 152.85 g. portion of p-chlorophenol and 56.1 g. of potassium hyroxide are stirred and heated to 150°–160° C. in an oil bath. When solution is complete the mixture is cooled to 100°–110° C. and 0.5 g. of activated copper powder (prepared by treating copper powder with 5% hydrochloric acid, washing with water, acetone and ether and drying at 100° C. for 15 minutes) is added. A 67.2 g. portion of 1,4-dichloro-2-nitrobenzene is added and the mixture is heated to 170°–180° C. in an oil bath to start the reaction. The oil bath is removed until the reaction subsides, a second 67.2 g. portion of 1,4-dichloro-2-nitrobenzene is added, the mixture is heated to 180° C. for 30–60 minutes, cooled, water is added and the product is extracted in ether. The ether is washed, dried and evaporated giving an oil which is crystallized from methanol, giving 4-chlorophenyl-4-chloro-2-nitrophenyl ether.

A 140 g. portion of the above nitro derivative in 1400 ml. of acetone is reduced with 560 g. of sodium hydrosulfite in 1400 ml. of water as described in Example 1, giving 5-chloro-2-(p-chlorophenoxy)aniline.

A mixture of 43.6 g. of isonicotinic acid, 200 ml. of thinyl chloride and 200 ml. of methylene chloride is heated under reflux for 2 hours. The solvent is evaporated, 93.4 g. of 5-chloro-2-(p-chlorophenoxy)aniline, 180.0 g. of anhydrous potassium carbonate and 2800 ml. of benzene are added and the reaction proceeds as described in Example 1. Extraction with petroleum ether gives 5′-chloro-2′-(p-chlorophenoxy)-isonicotinanilide.

A 100 g. portion of the preceding compound is added to 125 g. of phosphorous pentoxide and 750 ml. of phosphorous oxychloride and reacted as described in Example. 1. The residue obtained by evaporation of the methylene chloride extracts is 2,8-dichloro-11-(4-pyridyl)-dibenz[b,f][1,4]oxazepine, mp. 214°–215° C.

A 20 ml. portion of methyl iodide is added to a solution of 10.0 g. of the preceding compound in 40 ml. of methylene chloride and reacted as described in Example 1, giving 4-(2,8-dichlorodibenz[b,f][1,4]oxazepin-11-yl)-1-methylpyridinium iodide, mp. 249°–250° C.

EXAMPLE 3

8-Chloro-10,11-dihydro-2-methoxy-11-(4-pyridyl)-dibenz[b,f][1,4]oxazepine and 4-(8-chloro-10,11-dihydro-2-methoxydibenz[b,f][1,4]oxazepin-11-yl)-1-methylpyridinium iodide A 5.0 g. portion of 8-chloro-2-methoxy-11-(4-pyridyl)-dibenz[b,f][1,4]oxazepine (Example 1) is added to 2.5 g. of lithium aluminum hydride in 200 ml. of ether. The mixture is stirred and heated under reflux for 4 hours. Water is added dropwise to decompose the excess lithium aluminum hydride. The ether is decanted and the residue is extracted with methylene chloride which is then combined with the ether, dried and evaporated. The residue is crystallized from acetone-hexane giving 8-chloro-10,11-dihydro-2-methoxy-11-(4-pyridyl)-dibenz[b,f][1,4]oxazepine, mp. 186°–188° C.

A 14.5 g. portion of the above compound is reacted with 29 ml. of methyl iodide in 58 ml. of methylene chloride as described in Example 1 giving 4-(8-chloro-10,11-dihydro-2-methoxydibenz[b,f][1,4]oxazepin-11-yl)-1-methylpyridinium iodide, mp. 240°–242° C.

EXAMPLE 4

2,8-Dichloro-10,11-dihydro-11-(4-pyridyl)-dibenz[b,f][1,4]oxazepine and 4-(2,8-Dichloro-10,11-dihydrodibenz[b,f][1,4]oxazepin-11-yl)-1-methylpyridinium iodide A 20.0 g. portion of 2,8-dichloro-11-(4-pyridyl)-dibenz[b,f][1,4]oxazepine (Example 2), 10.0 g. of lithium aluminum hydride and 800 ml. of ether are reacted as described in Example 3, giving 2,8-dichloro-10,11-dihydro-11-(4-pyridyl)dibenz[b,f][1,4]oxazepine, mp. 202°–205° C.

A 12.0 g. portion of the above compound is reacted with 24 ml. of methyliodide in 48 ml. of methylene chloride as described in Example 1, giving 4-(2,8-dichloro-10,11-dihydrodibenz[b,f][1,4]oxazepin-11-yl)-1-methylpyridinium ioidde, mp. 248°–250° C.

EXAMPLE 5

8-Chloro-11-(4-pyridyl)-dibenz[b,f][1,4]oxazepine and 4-(8-Chlorodibenz[b,f][1,4]oxazepin-11-yl)-1-methylpyridinium iodide A 100 ml. portion of thionyl chloride is added dropwise to 28.0 g. of isonicotinic acid over 30 minutes. After an additional 30 minutes the mixture becomes honogeneous. The volatiles are removed in vacuo, 250 ml. of benzene is added and then removed to leave a residue. This residue is suspended in 300 ml of dry tetrahydrofuran and a solution of 25.0 g. of 5-chloro-2-phenoxyaniline in 63 ml. of triethylamine is added dropwise over 30 minutes and the mixture is stirred overnight. The mixture is poured into 500 ml. of 1 N-sodium hydroxide. The organic layer is separated. The basic layer is extracted with two 100 ml. portions of ether. The ether extracts and organic layer are combined, washed with 250 ml. of water and then with four 200 ml. portions of 10% hydrochloric acid. The combined acid washings are neutralized with concentrated ammonium hydroxide and extracted with three 250 ml. portions of ether. These ether extracts are dried and evaporated giving 5′-chloro2′-phenoxy-isonicotinanilide as a brown solid.

A 31.98 g. portion of the above compound is combined with 43 g. of phosphorous pentoxide and 300 ml. of phosphorous oxychloride and heated at reflux overnight. The excess phosphorous oxychloride is removed by distillation and the residue is poured onto a mixture of 100 ml. of concentrated ammonium hydroxide and 500 g. of ice. The mixture is extracted with three 250 ml. portions of methylene chloride. The extracts are dried and evaporated to a yellow solid which is crystallized from chloroform-hexane, giving 8-chloro-11-(4-pyridyl)dibenz[b,f][1,4]oxazepine, mp. 122°–122.5° C.

A 5.46 g. portion of the previous compound and 19.6 g. of methyl iodide in 100 ml. of acetone are heated at reflux for 30 minutes. An additional one gram of methyl iodide is added and heating is continued for 30 minutes. The mixture is cooled, filtered and the solid is dried, giving 4-(8-chlorodibenz[b,f][1,4]oxazepin-11-yl)-1-methylpyridinium iodide as a yellow solid, mp. 238°–243° C.

The foregoing examples are merely illustrative of the invention which is limited solely by the claims. Other embodiments of this invention will be obvious to those skilled in the art without departing from the spirit of the invention.

We claim:

1. A compound of the formula:

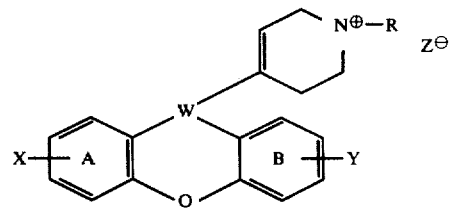

wherein phenyl rings A and B may be unsubstituted, mono-, di- or trisubstituted and X and Y are each selected from the group consisting of hydrogen, halogen, lower alkyl ($C_1$–$C_6$), lower alkoxy ($C_1$–$C_6$), methylthio trifluoromethyl, nitro, amino and di(lower)alkylsulfamoyl; Z is selected from the group consisting of chlorine, bromine and iodine; R is selected from the group consisting of lower alkyl (C₁-C₆), hydroxy lower alkyl, propargyl,

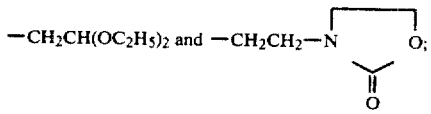

W is selected from the group consisting of

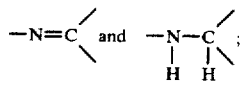

and the pharmaceutically acceptable salts thereof.

2. The compound of claim 1, of the formula:

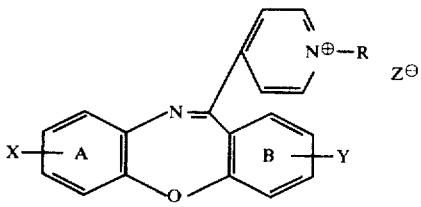

wherein phenyl rings A and B are unsubstituted, mono-, di- or trisubstituted and X and Y are each selected from the group consisting of hydrogen, halogen, lower alkyl (C₁-C₆), lower alkoxy (C₁-C₆), methylthio, trifluoromethyl, nitro, amino and di(lower)alkylsulfamoyl; Z is selected from the group consisting of chlorine, bromine and iodide; and R is selected from the group consisting of lower alkyl (C₁-C₆), hydroxy lower alkyl, propargyl,

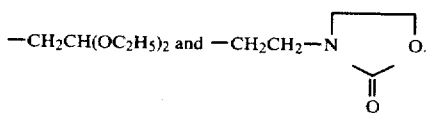

3. The compound of claim 1, of the formula:

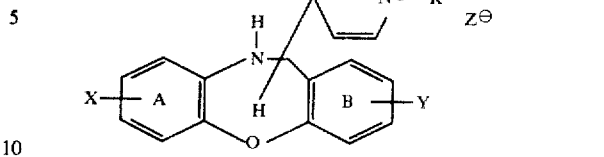

wherein phenyl rings A and B are unsubstituted, mono-, di- or trisubstituted and X and Y are each selected from the group consisting of hydrogen, halogen, lower alkyl (C₁-C₆), lower alkoxy (C₁-C₆), methylthio, trifluoromethyl, nitro, amino and di-(lower)alkylsulfamoyl; Z is selected from the group consisting of chlorine, bromine and iodine; and R is selected from the group consisting of lower alkyl (C₁-C₆), hydroxy lower alkyl, propargyl,

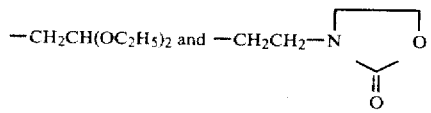

4. The compound of claim 1, 8-Chloro-2-methoxy-11-(4-pyridyl)-dibenz[b,f][1,4]oxazepine.

5. The compound of claim 1, 4-(8-Chloro-2-methoxydibenz[b,f][1,4]oxazepin-11-yl)-1-methylpyridinium iodide.

6. The compound of claim 1, 2,8-Dichloro-11-(4-pyridyl)-dibenz[b,f][1,4]oxazepine.

7. The compound of claim 1, 4-(2,8-Dichloro-dibenz[b,f][1,4]oxazepin-11-yl)-1-methylpyridinium iodide.

8. The compound of claim 1, 8-chloro-1-10,11-dihydro-2-methoxy-11-(4-pyridyl)-dibenz[b,f][1,4]oxazepine.

9. The compound of claim 1, 4-(8-Chloro-10,11-dihydro-2-methoxydibenz[b,f][1,4]oxazepin-11-yl)-1-methylpyridinium iodide.

10. The compound of claim 1, 2,8-Dichloro-10,11-dihydro-11-(4-pyridyl)-dibenz[b,f][1,4]oxazepine.

11. The compound of claim 1, 4-(2,8-Dichloro-10,11-dihydrodibenz[b,f][1,4]oxazepin-11-yl)-1-methylpyridinium iodide.

12. The compound of claim 1, 8-Chloro-11-(4-pyridyl)-dibenz[b,f][1,4]oxazepine.

13. The compound of claim 1, 4-(8-Chlorodibenz[b,f][1,4]oxazepin-11-yl)-1-methylpyridinium iodide.

14. The compound of claim 1, 8-Chloro-10,11-dihydro-11-(4-pyridyl)-dibenz[b,f][1,4]oxazepine.

* * * * *